(12) United States Patent
Baek

(10) Patent No.: US 9,598,394 B2
(45) Date of Patent: Mar. 21, 2017

(54) METHOD OF PRODUCING TRIOXANE

(71) Applicant: Sung Yong Baek, Ulsan (KR)

(72) Inventor: Sung Yong Baek, Ulsan (KR)

( * ) Notice: Subject to any disclaimer, the term of this patent is extended or adjusted under 35 U.S.C. 154(b) by 0 days.

(21) Appl. No.: 14/817,736

(22) Filed: Aug. 4, 2015

(65) Prior Publication Data

US 2016/0075679 A1    Mar. 17, 2016

(30) Foreign Application Priority Data

Sep. 16, 2014    (KR) .................. 10-2014-0122844

(51) Int. Cl.
*C07D 323/06*    (2006.01)
(52) U.S. Cl.
CPC .................. *C07D 323/06* (2013.01)
(58) Field of Classification Search
CPC .................................................. C07D 323/06
See application file for complete search history.

(56) References Cited

U.S. PATENT DOCUMENTS 8,981,125 B2    3/2015    Cho et al.

FOREIGN PATENT DOCUMENTS

| EP | 0583907 A2 | 2/1994 |
|---|---|---|
| JP | S57200383 A | 12/1982 |
| JP | H0673046 A | 3/1994 |
| KR | 101092220 B1 | 12/2011 |

OTHER PUBLICATIONS

Cho et al., 2004, caplus an 2004:950140.*
Siegert et al., 2006, caplus an 2006:388087.*
Korea Patent Application 10-2014-0122844, Office Action, Oct. 30, 2014 (including English Translation), 7 pages.
Korea Patent Application 10-2014-0122844, Notice of Allowance, Feb. 3, 2015 (including English Translation), 3 pages.

* cited by examiner

*Primary Examiner* — Sun Jae Yoo
(74) *Attorney, Agent, or Firm* — Abelman, Frayne & Schwab

(57) ABSTRACT

Disclosed is a method of producing trioxane, including: (A) preparing trioxane from a high-concentration formaldehyde aqueous solution in the presence of an acid catalyst; (B) distilling a mixture including trioxane; (C) liquefying the distilled gas mixture; (D) mixing the liquefied liquid mixture with an extraction solvent and separating the mixture into an aqueous phase and a solvent phase; (E) distilling the solvent phase to give trioxane, and mixing the aqueous phase with the extraction solvent to give a mixture, which is then separated into an aqueous phase and a solvent phase; and (F) discharging the aqueous phase separated in (E) out of the system, and recirculating the solvent phase so as to be reused in (D) and (E).

17 Claims, 3 Drawing Sheets

METHOD OF PRODUCING TRIOXANE

CROSS-REFERENCE TO RELATED APPLICATION

This application claims the benefit of Korean Patent Application No. 10-2014-0122844, filed Sep. 16, 2014, entitled "Process for producing trioxane", which is hereby incorporated by reference in its entirety into this application.

BACKGROUND OF THE INVENTION

1. Technical Field

The present invention relates to a method of producing trioxane.

2. Description of the Related Art

Polyoxymethylene, which is an engineering plastic, is prepared from trioxane. A variety of trioxane synthesis methods have been known to date. In particular, synthesis of trioxane by heating formaldehyde in the presence of an acid catalyst is mainly utilized.

Without regard to the synthesis methods, trioxane is obtained in the form of, not a pure material, a mixture comprising formaldehyde, small amounts of other components (e.g. methanol, methyl formate, methyl aldehyde and formic acid), and a large amount of water. Pure trioxane is required to prepare polyoxymethylene. To this end, diverse processes such as distillation, extraction, distillative extraction, and pressure swing distillation are disclosed.

As for production of trioxane using distillation evaporation, a large amount of water is inevitably contained due to vapor-liquid equilibrium of trioxane-formaldehyde-water. Since evaporation of water is accompanied by a loss of a very large amount of evaporation heat, the energy necessary for production of trioxane is increased.

To reuse some of the energy consumed as the evaporation heat, Korean Patent Application No. 2010-0107119 and Japanese Patent Application No. 1981-084832 disclose a method of extracting trioxane with an organic solvent from a gaseous distillate via distillative extraction. However, these patents are problematic because the mixture comprising trioxane, formaldehyde, and water, with latent heat, is fed in a gas phase into an extraction column, making it impossible to utilize latent heat as energy.

Separation of trioxane from the gas mixture comprising trioxane, formaldehyde, and water needs a large amount of energy to undergo a phase change. Hence, Japanese Patent Application No. 1992-208265 discloses a method of extracting trioxane synthesized in the presence of a solid catalyst, using a solvent having a boiling point higher than that of trioxane, without the use of a distillation column, namely, without phase change. However, trioxane, which has high solubility in water, may remain, to a large degree, in an aqueous phase. To reduce the amount of trioxane in an aqueous phase, Japanese Patent Application No. 1992-208265 discloses the use of at least 2800 ml of a solvent to extract 1 g of trioxane. When a large amount of solvent is employed in this way, a large-sized distillation column is required for the subsequent process for separating trioxane and the solvent, and a great amount of energy is also consumed.

For conventional separation of the mixture comprising formaldehyde, water, and trioxane, phase change into a gas phase and then distillation are performed. As such, a large amount of energy is undesirably consumed during phase change. Furthermore, the case where liquid/liquid extraction is carried out without phase change is problematic because a large amount of trioxane is transferred to an aqueous phase, undesirably deteriorating processing efficiency.

SUMMARY OF THE INVENTION

Therefore, an aspect of the present invention is to provide a method of efficiently and profitably producing trioxane, wherein energy used for reaction and evaporation is recovered through energization of a gas mixture discharged from the top of a distillation column, and a liquid mixture comprising formaldehyde, water, and trioxane liquefied through energization is passed through two liquid/liquid extractors connected in series, thus decreasing the discharge of trioxane into an aqueous phase.

In order to accomplish the above aspect, an embodiment of the present invention provides a method of producing trioxane, comprising: (A) preparing trioxane from a formaldehyde aqueous solution in the presence of an acid catalyst; (B) distilling a mixture including trioxane; (C) liquefying the distilled gas mixture; (D) mixing the liquefied liquid mixture with an extraction solvent and separating the mixture into an aqueous phase and a solvent phase; (E) distilling the solvent phase to give trioxane, and mixing the aqueous phase with the extraction solvent to give a mixture, which is then separated into an aqueous phase and a solvent phase; and (F) discharging the aqueous phase separated in (E) out of the system, and recirculating the solvent phase so as to be reused in (D) and (E).

According to an embodiment of the present invention, a method of producing trioxane enables 80~85% of energy consumed in reactors and distillation columns for use in trioxane synthesis to be recovered in a steam, thus achieving energy consumption reduction, and can solve problems with low extraction efficiency caused by incorporation of a large amount of trioxane into an aqueous phase upon liquid/liquid extraction, ultimately increasing the trioxane yield. Furthermore, solvents having various boiling points can be used depending on the process conditions, regardless of the azeotropic point of water and trioxane.

BRIEF DESCRIPTION OF THE DRAWINGS

The above and other aspects, features and advantages of the present invention will be more clearly understood from the following detailed description taken in conjunction with the accompanying drawings, in which.

DESCRIPTION OF SPECIFIC EMBODIMENTS

The present invention can be achieved by the following description, which is set forth to illustrate but is not construed to limit the present invention. Furthermore, the appended drawings are provided for clarity, and the present invention is not limited thereto, and details of the individual components thereof can be properly understood by the specific effects of the relevant description, which will be described later.

Figure 1:
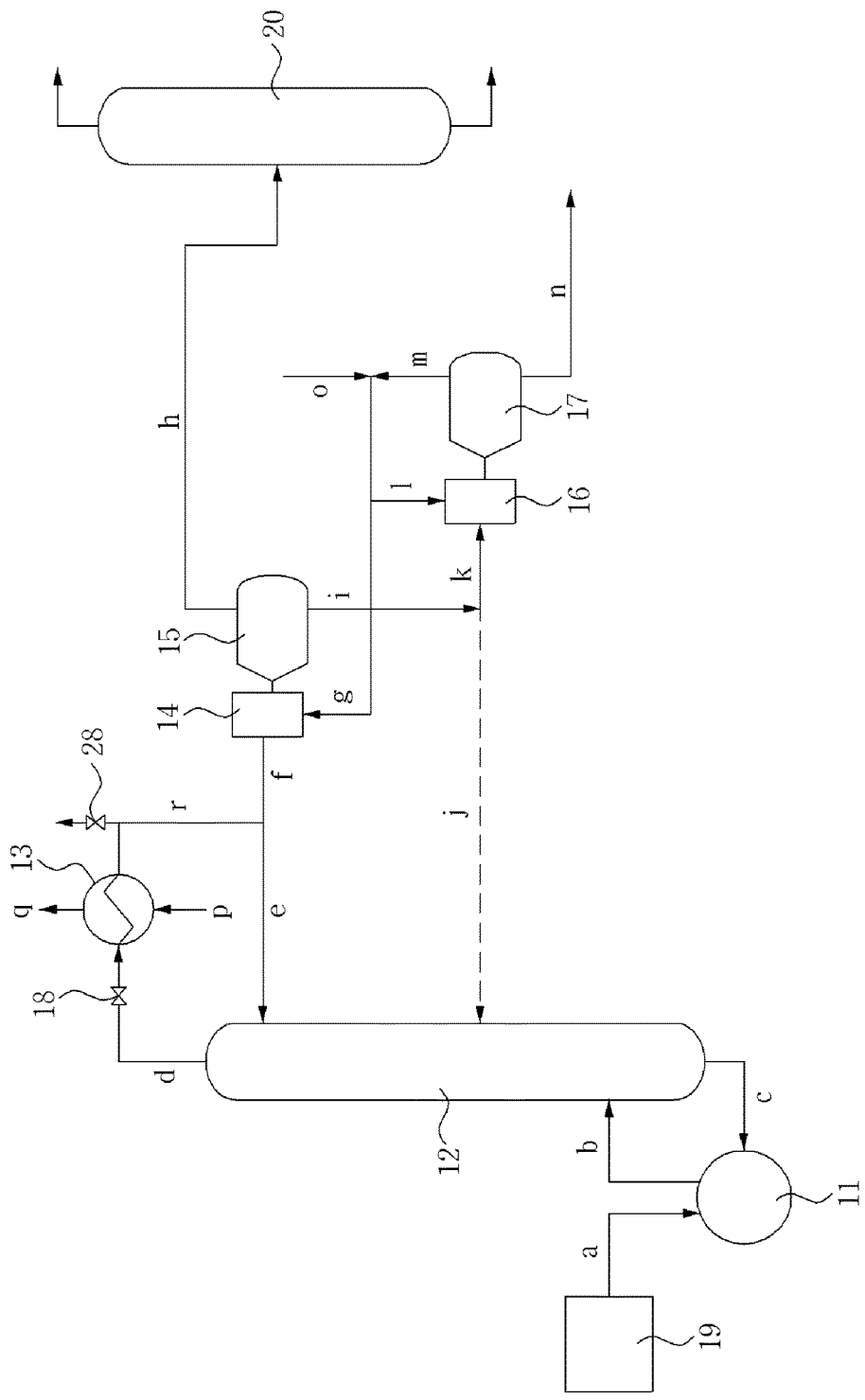
FIG. 1 illustrates a process of producing trioxane according to an embodiment of the present invention.

Hereinafter, a detailed description will be given of a method of producing trioxane according to an exemplary embodiment of the present invention. Referring to FIG. 1, units and process streams for individual steps according to the present invention are described.

Specifically, preparing trioxane from a formaldehyde aqueous solution in the presence of an acid catalyst includes concentrating formaldehyde to give a high-concentration formaldehyde aqueous solution, which is then allowed to react in the presence of an acid catalyst, giving trioxane.

of the distillation column is determined by the azeotropic point of water and trioxane. The azeotropic points of water and trioxane are summarized in Table 1 below. As shown in Table 1, the azeotropic point of water and trioxane at about 760 mmHg (1 atm) is about 92.4° C. When the top of the distillation column is at 760 mmHg, the temperature of the top of the distillation column is about 92.4° C.

TABLE 1

Azeotropic point of azeotrope depending on pressure

| | Pressure Azeotrope | | | | | | | | | |
|---|---|---|---|---|---|---|---|---|---|---|
| | 600 (mmHg) | 760 (mmHg) | 830 (mmHg) | 935 (mmHg) | 950 (mmHg) | 1,100 (mmHg) | 1,500 (mmHg) | 1,875 (mmHg) | 2,250 (mmHg) | 3,000 (mmHg) |
| Trioxane-Water | 86.0° C. | 92.4° C. | 94.9° C. | 98° C. | 98.7° C. | 103° C. | 112.2° C. | 119.9° C. | 126.1° C. | 135.9° C. |
| Benzene-Water | 62.5° C. | 69.2° C. | 71.7° C. | 74.8° C. | 75.6° C. | 79.8° C. | 89.4° C. | 96.4° C. | 102.6° C. | 112.6° C. |

The concentration of the formaldehyde aqueous solution is adjusted to be high using a concentrator 19. Such a formaldehyde aqueous solution has as high a concentration as about 40~85 wt %. If the concentration of the formaldehyde solution is less than about 40 wt %, conversion from formaldehyde into trioxane may decrease, and the amount of water that should be discharged out of the system via distillation may increase, undesirably resulting in low processing efficiency. The concentration of the formaldehyde aqueous solution useful in typical trioxane preparation is about 55~80 wt %, and particularly about 60~75 wt %.

The high-concentration formaldehyde aqueous solution concentrated in the concentrating step is transferred to a reactor 11 to produce trioxane in the presence of an acid catalyst. The reaction in the reactor is carried out by heating the high-concentration formaldehyde aqueous solution in the presence of an acid catalyst. A gas mixture containing trioxane is produced via the reaction in the reactor. The gas mixture contains unreacted formaldehyde, water, and produced trioxane. More specifically, the gas mixture contains about 12~16 wt % of trioxane. The acid catalyst for use in the above reaction may be a homogeneous catalyst, or a solid acid catalyst. In an embodiment, the acid catalyst may include an inorganic acid catalyst, such as sulfuric acid and phosphoric acid; an organic acid catalyst, such as sulfonic acid, phosphonic acid, and trifluoroacetic acid; a solid acid catalyst, such as a strong acidic cation exchange resin, zeolite, silica, alumina, and activated clay; or a heteropoly acid catalyst, such as phosphorus molybdate or phosphorus tungstate. In an embodiment, when the solid acid catalyst is used, it is fed in a liquid phase into a distillation column so that distillation is carried out, thus obtaining a gas mixture.

The gas mixture containing trioxane is supplied into a first distillation column 12 from the reactor so that distillation is carried out. The distilling step is a process for increasing the concentration of trioxane contained in the gas mixture. In an embodiment, the gas mixture comprising about 17~35 wt % of formaldehyde, about 20~50 wt % of water, and about 20~55 wt % of trioxane is discharged from the top of the distillation column through distillation. Moreover, taking into consideration the processing efficiency, the concentration of trioxane of the gas mixture is favorably set to about 35 wt % or more.

In the top of the distillation column, water and trioxane are formed into an azeotrope, and the temperature of the top The azeotropic gas mixture containing formaldehyde, water, and trioxane is supplied to a steam generator 13 from the top of the distillation column so that liquefaction is carried out. In the liquefying step, pure water placed in the steam generator is produced into a steam using latent heat of the gas mixture, and the gas mixture from which latent heat was lost is liquefied. As the temperature of the top of the distillation column, namely, the temperature of the gas mixture, is higher, vaporization of pure water becomes favorable. The temperature and pressure of the top of the distillation column show the following behavior in a vapor phase depending on vapor-liquid equilibrium of formaldehyde-water-trioxane.

When the pressure of the top of the distillation column is high, the azeotropic point of water-trioxane may increase, thus raising the pressure of the recovered steam. However, as the concentration of formaldehyde in a gas phase is increased on the vapor-liquid equilibrium plane of formaldehyde-water, the amount of formaldehyde discharged out of the system is undesirably increased. On the other hand, when the pressure of the top thereof is low, the azeotropic point of water-trioxane may decrease, thus lowering the pressure of the recovered steam, and thereby a steam should be generated in a vacuum. However, as the concentration of formaldehyde in a vapor phase is decreased on the vapor-liquid equilibrium plane of formaldehyde-water, the amount of formaldehyde discharged out of the system is decreased and water may be quickly removed. Briefly, since the gas mixture of formaldehyde-water-trioxane is used as a heat source of the steam generator for converting pure water into a steam, the temperature of the gas mixture is regarded as important in terms of determining the pressure of generated steam and the amount of formaldehyde discharged out of the system.

In the course of converting pure water into a steam, the use of latent heat of a vapor phase lower than 100° C. results in generation of a steam at 760 mmHg (1 atm) or less. If the temperature of the vapor phase serving as a heat source is remarkably lower than 100° C., for example, when the vapor of a benzene-water azeotrope (about 69° C. at a pressure of 760 mmHg in Table 1) generated at the top of the distillation column upon distillation extraction of Comparative Example 1 is used as a heat source, a desired steam is not profitably formed. Briefly, distillative extraction makes it difficult to recover energy with the steam. In an embodiment, the pressure of the steam formed by the steam generator is about 250~1700 mmHg, particularly about 280~1200 mmHg, and more particularly about 300~1000 mmHg.

As mentioned above, since the temperature of the top of the distillation column is affected by the pressure of the top of the distillation column, the pressure of the top of the distillation column has to be increased to raise the steam temperature of the top thereof. In an embodiment, two pressure control valves 18, 28 may be provided to regulate desired pressure and temperature. One pressure control valve 18 is positioned upstream of the steam generator, and the other pressure control valve 28 is positioned downstream of the vapor generator, in order to regulate the pressure. To increase the pressure of the top of the distillation column, the first valve 18 positioned upstream of the steam generator is used, and the second valve 28 positioned downstream of the steam generator is used to reduce the pressure of the top of the distillation column In an embodiment, the pressure of the top of the distillation column is about 600~3000 mmHg, particularly about 600~2000 mmHg, and more particularly about 700~1800 mmHg.

The gas mixture comprising formaldehyde, water, and trioxane, which is discharged from the top of the distillation column in the distilling step, is fed into the steam generator 13. The steam generator functions to cool the gas mixture comprising formaldehyde, water, and trioxane to form a liquid mixture, and also functions to convert pure water fed through the stream p of FIG. 1 into a steam. The solubility of trioxane in water is at least 100 g trioxane/100 g water at about 60° C. or higher. However, since the solubility is lowered with a decrease in the temperature, the temperature of the liquid mixture should be controlled so as to prevent precipitation of trioxane.

The steam generator may be a kettle type heat exchanger or a plate type heat exchanger in combination with a knock-out drum, but the present invention is not limited thereto.

The liquid mixture liquefied using the steam generator is mixed with an extraction solvent and then separated into an aqueous phase and a solvent phase. Specifically, some of the liquid mixture liquefied using the steam generator may be refluxed to the top of the first distillation column 12, and the remainder thereof is mixed with the extraction solvent using a mixer 14 and then fed into a first liquid/liquid extractor 15. As the extraction solvent, any solvent typically useful in the art may be employed so long as it is immiscible with water and has higher trioxane solubility than that of water. Examples of the extraction solvent may include benzene, ethylene dichloride, chloroform, chlorobenzene, dichlorobenzene, trichlorobenzene, diethylbenzene, xylene, and ethylbenzene.

The liquid mixture containing the solvent placed in the first liquid/liquid extractor 15 via the mixer 14 is separated into a solvent phase and an aqueous phase. The liquid in a solvent phase is transferred to a second distillation column 20 through the stream h, thus obtaining pure trioxane by distillation. On the other hand, the liquid in an aqueous phase is refluxed again to the first distillation column 12 through the stream i, or is mixed with the solvent and then fed into a second liquid/liquid extractor 17. The stream j where the liquid in an aqueous phase discharged from the first liquid/liquid extractor is refluxed again to the first distillation column may not be carried out. Unless the stream j is conducted, a large amount of unreacted formaldehyde is contained in the aqueous phase of the second liquid/liquid extractor and may thus be undesirably discharged out of the system, but the selection range of the extraction solvent becomes wide. As such, an extraction solvent having a boiling point equal to or higher than the azeotropic point of water and trioxane may be selectively used. On the other hand, when the aqueous phase of the first liquid/liquid extractor is refluxed to the first distillation column through the stream j, the amount of unreacted formaldehyde discharged out of the system may be decreased, but a solvent having a boiling point lower than the azeotropic point of water and trioxane should be selected. This is because, when a small amount of solvent contained in the aqueous phase of the first liquid/liquid extractor is added to the first distillation column by refluxing, the solvent having a boiling point higher than the azeotropic point of water and trioxane is not boiled but may accumulate on the bottom of the distillation column In an embodiment, when the stream j is carried out, the extraction solvent is desirably benzene.

As mentioned above, some or all of the aqueous phase of the first liquid/liquid extractor may be mixed with the extraction solvent in the second mixer 16 and then fed into the second liquid/liquid extractor 17, after which the liquid mixture including the solvent fed into the second liquid/liquid extractor is further separated into a solvent phase and an aqueous phase. As such, the aqueous phase thus separated is discharged out of the system, and the solvent phase is combined with the extraction solvent fed from the outside and then placed in the first mixer so as to be fed into the first liquid/liquid extractor, or is fed into the second mixer so as to be added to the second liquid/liquid extractor. Actually, the extraction solvent, which is fed into the first and the second mixer, is composed of the stream o returning from the second distillation column 20 and the stream m discharged to the solvent phase of the liquid/liquid extractor. These two streams are combined, and then placed in the first mixer through the stream g and also in the second mixer through the stream l. The amount of the extraction solvent fed into the second mixer through the stream l should be greater than the amount of the extraction solvent fed into the first mixer through the stream g, and the ratio thereof may vary depending on the concentration and amount of the aqueous phase separated by the first liquid/liquid extractor.

In an embodiment of the present invention, trioxane is separated from the liquid mixture comprising formaldehyde, water, and trioxane, using two liquid/liquid extractors. The number of liquid/liquid extractors, which are used to increase extraction efficiency of trioxane, is not limited to two. Table 2 below shows the distribution coefficient K when using a single liquid/liquid extractor and when continuously using two liquid/liquid extractors. The distribution coefficient K is defined as represented by Equation 1 below.

$$K = \frac{\text{Concentration of trioxane in solvent phase in equilibrium}}{\text{Concentration of trioxane in aqueous phase in equilibrium}} \quad \text{[Equation 1]}$$

TABLE 2

Distribution coefficient depending on solvent and number of extractors

| | Solvent | |
| Number of extractors | Benzene | Dichlorobenzene |
| --- | --- | --- |
| One extractor | 1.6~2.2 | 0.7~1.7 |
| Two extractors | 3< | 2.5< |

(*The distribution coefficient upon using two extractors is calculated by dividing the concentration of trioxane in a solvent phase of the first liquid/liquid extractor in equilibrium by the concentration of trioxane in an aqueous phase of the second liquid/liquid extractor in equilibrium.)

As is apparent from Table 2, when using two liquid/liquid extractors compared to when using a single liquid/liquid extractor, a higher distribution coefficient may result, and problems with a large amount of trioxane present in an aqueous phase may be solved, thus increasing the extraction efficiency. In an embodiment, when two liquid/liquid extractors are used, the distribution coefficient may fall in the range of from about 2.2 to less than 50.

The first and the second mixer and the liquid/liquid extractor (mixer-settler type) may be used without limitation so long as they are useful in the art, and the type of liquid/liquid extractor is not limited.

The solvent phase discharged from the first liquid/liquid extractor is a liquid mixture comprising the extraction solvent and trioxane, and is fed into the second distillation column, so that pure trioxane is finally separated.

A better understanding of the present invention may be obtained through the following examples that are not to be construed as limiting the scope of the present invention.

EXAMPLES

Example 1

This example represents a process of producing trioxane through the process streams of FIG. 1. An apparatus used in this embodiment is depicted in FIG. 1, comprising: a 5 L heater-equipped reactor 11, a distillation column 12 having 30 sieve trays with an inner diameter of 50 mm, a kettle type steam generator 13, 1 L mixers 14, 16 with two-wing paddle agitators rotating at 800 rpm in maximum, and liquid/liquid extractors 15, 17.

A formaldehyde aqueous solution having a concentration of about 75 wt % using a concentrator 19 was fed into the reactor 11 at a rate of about 400 g/hr, and sulfuric acid was also placed in the reactor 11, so that the concentration of sulfuric acid was adjusted to about 2 wt %. A gas mixture including trioxane produced by heating a vapor at about 1450 g/hr was fed into the distillation column 12. Through distillation in the distillation column 12, a gas mixture comprising formaldehyde, water, and about 40 wt % of trioxane was obtained from the top of the distillation column. The gas mixture was a gas having a temperature of about 95° C. or more obtained by controlling the upper pressure of the distillation column 12 to about 830 mmHg using pressure control valves 18, 28, and was fed into the steam generator 13 through the stream d. In the steam generator 13, a vapor at about 400 mmHg was produced in about 1230 g/hr. Some of a liquid mixture comprising formaldehyde, water, and trioxane, liquefied by the steam generator, was refluxed to the top of the distillation column 12 through the stream e, and the remainder was fed at about 730 g/hr into the mixer 14 through the stream f. Also, about 775 g/hr of the benzene solution stream g was fed into the mixer 14, in which such a benzene solution stream was obtained by combining the benzene solution resulting from distillation in the distillation column 20 corresponding to the stream o with the benzene solvent phase of the liquid/liquid extractor 17 corresponding to the stream m. The resulting mixture was fed from the mixer into the liquid/liquid extractor 15 and then separated into a benzene solvent phase and an aqueous phase. The solution of the separated benzene solvent phase was fed into the distillation column 20 through the stream h, and thereby benzene and trioxane were obtained from the top and the bottom of the distillation column, respectively. About 345 g/hr of the aqueous phase separated from the liquid/liquid extractor 15 was returned to the distillation column 12 through the stream j, and about 173 g/hr of the remainder was fed into the mixer 16 through the stream k. In the mixer 16, about 1240 g/hr of the benzene solution was placed, and then mixed with the aqueous phase supplied through the stream k, and then finally fed into the liquid/liquid extractor 17. Such a mixture was separated into a benzene solvent phase and an aqueous phase by the liquid/liquid extractor 17, after which the benzene solvent phase was recirculated through the stream m, and about 152 g/hr of the aqueous phase was discharged out of the system through the stream n. The distribution coefficient of the first liquid/liquid extractor 15 was 1.79, and the distribution coefficient was further increased to 7.0 when using the second liquid/liquid extractor 17.

To obtain 1 g of trioxane in Example 1, about 6.2 g of the steam was used, but about 5.2 g of the steam was recovered by the steam generator 13. About 1.0 g of the steam was used, except for the recovered steam.

Example 2

Using the same apparatus as in Example 1, an about 60 wt % formaldehyde aqueous solution was placed in the reactor 11 at a rate of about 400 g/hr. Procedures were performed without the stream j where the aqueous phase separated in the liquid/liquid extractor 15 was returned to the distillation column 12, and an extraction solvent was benzene having a boiling point lower than the azeotropic point of water and trioxane.

The catalyst concentration and the conditions of the top of the distillation column were the same as in Example 1, and about 1220 g/hr of a steam was used for reaction and distillation, and about 1020 g/hr of the steam was recovered by a steam generator. About 400 g/hr of a liquid mixture comprising formaldehyde, water, and trioxane was fed into the mixer 14 through the stream f. Further, about 468 g/hr of the benzene solution stream g was fed into the mixer 14, and mixed with the liquid mixture, after which the resulting mixture was separated into a solvent phase and an aqueous phase by the liquid/liquid extractor 15. Also, about 277 g/hr of the aqueous phase was fed into the mixer 16 through the stream k, mixed with about 2045 g/hr of the benzene solution, and then separated into a solvent phase and an aqueous phase by a liquid/liquid extractor 17. About 254 g/hr of the aqueous phase thus separated was discharged out of the system through the stream n. The distribution coefficient of the first liquid/liquid extractor 15 was 2.12, and the distribution coefficient was further increased to 5.94 when using the second liquid/liquid extractor 17.

To obtain 1 g of trioxane in Example 2, about 8.3 g of the steam was used, but about 7.0 g of the steam was recovered by the steam generator 13. About 1.3 g of the steam was used, except for the recovered vapor.

Comparative Example 1

Figure 2:
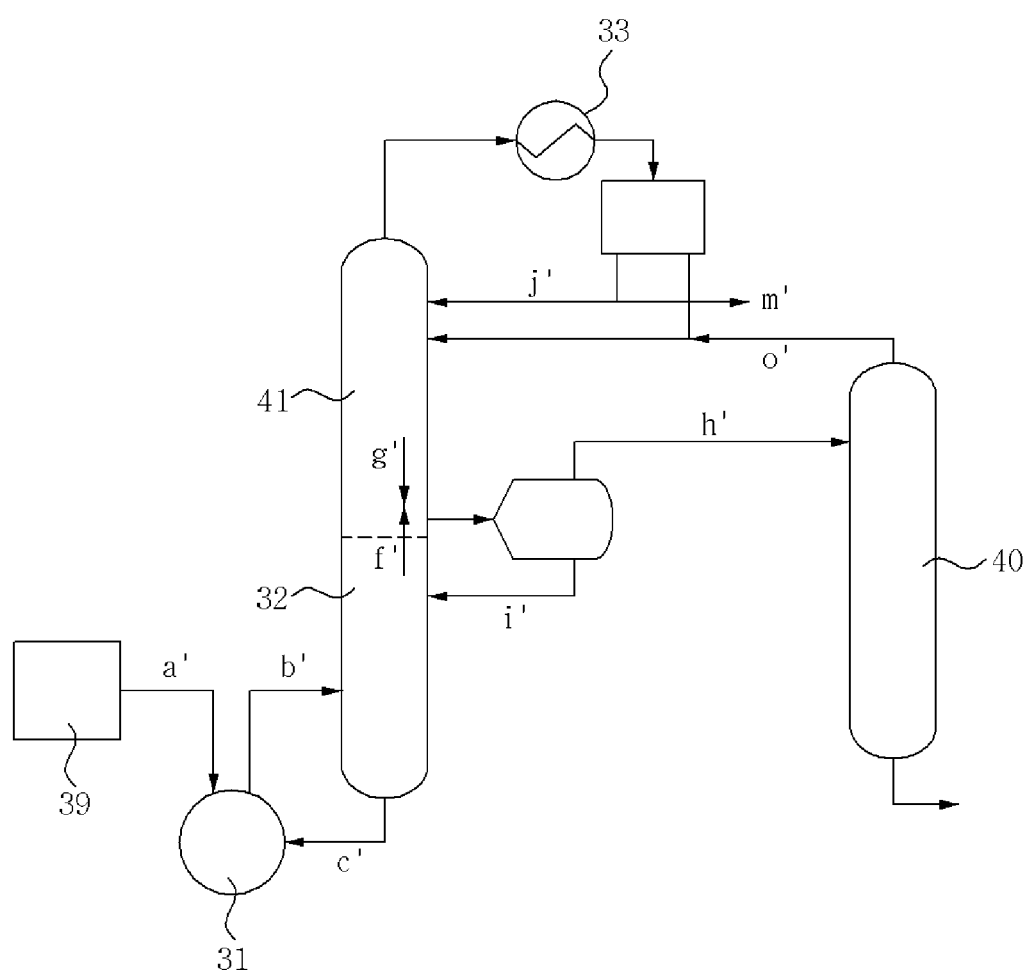
FIG. 2 illustrates a process of producing trioxane in Comparative Example 1.

Comparative Example 1 represents a process of producing trioxane through the process streams of FIG. 2. A distillation column 32+41 is provided in integrated form comprising a distillation unit 32 (column diameter: 30 mm, 15 trays) and an extraction unit 41 (column diameter: 50 mm, 20 trays). A reactor 31 and a catalyst were the same as those in Example 1, and an aqueous solution containing about 65 wt % formaldehyde was fed at about 400 g/hr into the reactor 31. The reactor 31 was heated using about 1400 g/hr of a high-temperature steam, thus producing a vapor containing trioxane, which was then fed into the distillation unit 32 of the extraction distillation column 32+41. An extraction solvent, namely, benzene, was fed through the stream o'. The vapor containing trioxane fed into the distillation unit 32 was introduced into the extraction unit 41, and discharged through the sidecut stream together with benzene supplied from the extraction unit 41, so that phase separation was carried out. About 620 g/hr of the separated benzene solvent phase h' was fed into the second distillation column 40, and thereby benzene was obtained from the top of the distillation column and trioxane was obtained from the bottom of the distillation column. The aqueous phase separated from the sidecut was recirculated to the distillation unit 32 through the stream i' to maintain the interface.

In the formaldehyde aqueous solution fed into the reactor, some of water was discharged out of the system through the stream m', and the remainder thereof was recirculated to the top of the extraction unit 41 through the stream j'. As such, the stream m' was maintained at about 162 g/hr, and the stream j' was maintained at about 300 g/hr.

To obtain 1 g of trioxane in Comparative Example 1, about 5.8 g of the steam was used, and there was no recovered steam.

Comparative Example 2

Figure 3:
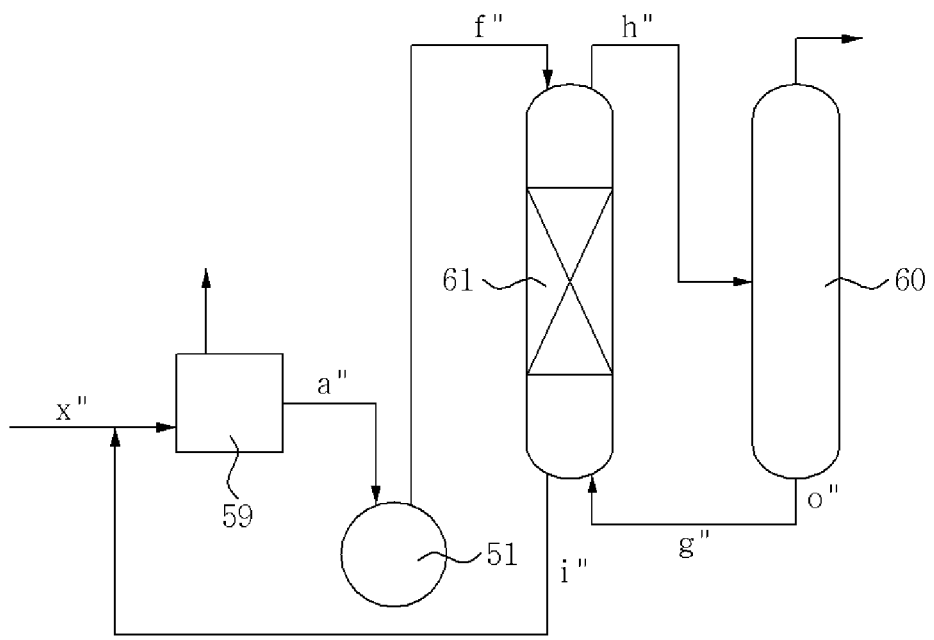
FIG. 3 illustrates a process of producing trioxane in Comparative Example 2.

Comparative Example 2 represents a process of producing trioxane through the process streams of FIG. 3. As illustrated in FIG. 3 for Comparative Example 2, used was an apparatus comprising: a 3 L distillation unit 59, a 300 cm$^3$ ion exchange resin-loaded reactor 51, a charging extraction column (inner diameter: 300 mm, height: 1.5 m) 61, and a distillation column 60 having an inner diameter of 300 mm with 40 sieve trays.

Specifically, an about 50 wt % formaldehyde aqueous solution was fed at about 100 g/hr through the stream x" and concentrated in the distillation unit 59 together with the material recovered from the extraction column 61. Next, the concentrated formaldehyde aqueous solution was transferred to the reactor 51 at about 95° C. through the stream a", thus obtaining a formaldehyde aqueous solution containing about 3.5 wt % of trioxane. Next, the aqueous solution obtained by the reactor was placed in the extraction column 61 through the stream f', and o-dichlorobenzene was fed into the extraction column 61 at a flow rate of about 3650 g/hr through the stream g", thereby extracting trioxane from the formaldehyde aqueous solution. The extract was fed into the distillation column 60 through the stream h" so as to be distilled. Consequently, about 43 g/hr of trioxane was obtained from the top of the distillation column 60.

To obtain 1 g of trioxane in Comparative Example 2, there was no steam used in the reactor.

TABLE 3

Data of Comparative Examples and Examples

| | | Ex. 1 | Ex. 2 | C. Ex. 1 | C. Ex. 2 |
|---|---|---|---|---|---|
| | Process Diagram | FIG. 1 | FIG. 1 | FIG. 2 | FIG. 3 |
| 1$^{st}$ Distillation column | Function | Distillation | Distillation | Distillation extraction | None |
| | Top pressure (mmHg) | 830 | 830 | 760 | Not applicable |
| | Top temp. (° C.) | 95 | 95 | 69 | Not applicable |
| Heat exchanger | Function | Vapor generation | Vapor generation | Cooler | Not applicable |
| | Feed | Pure water | Pure water | Cooling water | Not applicable |
| Energy recovery | Consumed steam (steam g/trioxane g) | 6.23 | 8.33 | 5.8 | Not applicable |
| | Recovered steam (steam g/trioxane g) | 5.26 | 7.03 | 0 | Not applicable |
| | Recovery ratio | 84% | 84% | 0% | Not applicable |
| | Consumed net steam (steam g/trioxane g) | 0.97 | 1.30 | 5.8 | 0 |
| Extractor | Fed mixture phase | Liquid | Liquid | Vapor | Liquid |
| | Solvent | Benzene | Benzene | Benzene | Dichlorobenzene |
| | Boiling point of solvent | Lower than azeotropic point of water and trioxane | Lower than azeotropic point of water and trioxane | Lower than azeotropic point of water and trioxane | Higher than boiling point of trioxane |
| | Amount of fed solvent mixture (1$^{st}$ extractor) | 775 g/hr | 468 g/hr | 390 g/hr | 3650 g/hr |
| | Amount of fed solvent mixture (2$^{nd}$ extractor) | 1240 g/hr | 2045 g/hr | None | None |
| | Aqueous phase reflux of 1$^{st}$ extractor | Some (j) | None | All (i') | All (i") |

Table 3 shows the data of Comparative Examples and Examples. In Comparative Example 1, distillation extraction was performed in a vapor phase but the gas mixture discharged from the top of the distillation column was at 69° C., making it difficult to recover pure water in the steam. In Comparative Example 2, energy consumption was small because of no phase change but a large amount of solvent was used in the extracting step, and thus a huge distillation column and a large amount of energy were required for the subsequent separation of the solvent and trioxane. However, in the present examples, the steam used for heating could be recovered again in the steam using pure water, thus increasing energy efficiency, and problems with to liquid/liquid extraction of Comparative Example 2 were solved using two liquid/liquid extractors connected in series.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of producing trioxane, comprising:
   (A) preparing trioxane from a formaldehyde aqueous solution in the presence of an acid catalyst;
   (B) distilling a mixture including trioxane, thus obtaining a distilled gas mixture;
   (C) liquefying the distilled gas mixture, thus obtaining a liquefied liquid mixture;
   (D) mixing the liquefied liquid mixture with an extraction solvent to give a mixture, which is then separated into an aqueous phase and a solvent phase;
   (E) distilling the solvent phase to give trioxane, and mixing the aqueous phase with the extraction solvent to give a mixture, which is then separated into an aqueous phase and a solvent phase; and
   (F) discharging the aqueous phase separated in (E) out of a system, and recirculating the solvent phase so as to be reused in (D) and (E),
   wherein before (C), a temperature of the gas mixture is adjusted via pressure control; in (C), pure water is converted into a steam to recover energy using latent heat of the gas mixture; and after (C), some of the liquefied liquid mixture is recirculated to (B), and
   the extraction solvent is a solvent that is immiscible with water and has trioxane solubility higher than that of water.

2. The method of claim 1, wherein the distilled gas mixture obtained in (B) comprises 20~55 wt % of trioxane.

3. The method of claim 1, wherein a pressure of the distilled gas mixture discharged in (B) ranges from 600 mmHg to 3000 mmHg.

4. The method of claim 1, wherein a pressure of the steam produced to recover energy in (C) ranges from 250 mmHg to 1700 mmHg.

5. The method of claim 1, wherein an amount of the extraction solvent added in (E) is greater than an amount of the extraction solvent added in (D).

6. The method of claim 1, wherein a distribution coefficient, indicating a ratio of a concentration of trioxane in the solvent phase separated in (D) and a concentration of trioxane in the aqueous phase separated in (E), is 2.2~50.

7. The method of claim 1, further comprising recirculating some of the aqueous phase to (B), after (D), wherein the extraction solvent used in (D) and (E) is an extraction solvent having a boiling point lower than an azeotropic point of trioxane and water.

8. A method of producing trioxane, comprising:
   preparing a mixture including trioxane from a formaldehyde aqueous solution in the presence of an acid catalyst;
   in a first distillation column, distilling the mixture including trioxane, thus obtaining a distilled gas mixture, wherein the first distillation column operates without extraction solvent;
   liquefying the distilled gas mixture by using latent heat thereof in a heat exchanger and recovering energy of the latent heat, thus obtaining a liquefied liquid mixture;
   mixing the liquefied liquid mixture with an extraction solvent in a first liquid/liquid extractor to produce a mixture, which is then separated into an aqueous phase and a solvent phase;
   in a second distillation column, distilling the solvent phase from the first liquid/liquid extractor to recover trioxane,
   mixing the aqueous phase from the first liquid/liquid extractor with the extraction solvent in a second liquid/liquid extractor to give a mixture, which is then separated into an aqueous phase and a solvent phase,
   wherein
      the aqueous phase from the second liquid/liquid extractor is discharged,
      the solvent phase is recycled to first liquid/liquid extractor and the second liquid/liquid extractor, and
      the extraction solvent is a solvent that is immiscible with water and has trioxane solubility higher than that of water.

9. The method of claim 8, wherein the temperature of the distilled gas mixture is adjusted by controlling pressure at the top of the first distillation column.

10. The method of claim 8, wherein the heat exchanger operates to receiver energy of the latent heat by converting a separate water stream into steam.

11. The method of claim 8, wherein a pressure of the steam produced to recover energy ranges from 250 mmHg to 1700 mmHg.

12. The method of claim 8, wherein the distilled gas mixture comprises 20~55 wt % of trioxane.

13. The method of claim 8, wherein a pressure of the distilled gas mixture ranges from 600 mmHg to 3000 mmHg.

14. The method of claim 8, wherein an amount of the extraction solvent added in the second liquid/liquid extractor is greater than an amount of the extraction solvent added in the first liquid/liquid extractor.

15. The method of claim 8, wherein a distribution coefficient, indicating a ratio of a concentration of trioxane in the solvent phase separated in the first liquid/liquid extractor and a concentration of trioxane in the aqueous phase separated in the second liquid/liquid extractor, is 2.2~50.

16. The method of claim 8, further comprising recirculating some of the aqueous phase from the first liquid/liquid extractor to the first distillation column.

17. The method of claim 16, wherein the extraction solvent is characterized by a boiling point lower than an azeotropic point of trioxane and water.

* * * * *